(12) United States Patent
Schade et al.

(10) Patent No.: US 11,191,947 B2
(45) Date of Patent: Dec. 7, 2021

(54) FLUID TREATMENT SYSTEM FOR A DRIVELINE CABLE AND METHODS OF ASSEMBLY AND USE

(71) Applicant: TC1 LLC, St. Paul, MN (US)

(72) Inventors: Christian Schade, Feldmeilen (CH); Justin Callaway, Goffstown, NH (US); Cori Pierce, Salem, NH (US)

(73) Assignee: TC1 LLC, St. Paul, MN (US)

( * ) Notice: Subject to any disclaimer, the term of this patent is extended or adjusted under 35 U.S.C. 154(b) by 175 days.

(21) Appl. No.: 16/218,971

(22) Filed: Dec. 13, 2018

(65) Prior Publication Data

US 2019/0201600 A1    Jul. 4, 2019

Related U.S. Application Data

(60) Provisional application No. 62/612,923, filed on Jan. 2, 2018.

(51) Int. Cl.
*A61M 60/857* (2021.01)
*A61M 39/02* (2006.01)
(Continued)

(52) U.S. Cl.
CPC ...... *A61M 60/857* (2021.01); *A61M 39/0247* (2013.01); *A61M 60/00* (2021.01);
(Continued)

(58) Field of Classification Search
CPC ...... A61M 2039/0282; A61M 39/0247; A61M 1/1008; A61M 1/127; A61M 1/1001; A61M 1/122; A61M 1/0058; A61M 39/0208; A61M 2039/0285; A61M 60/857; A61M 2039/0205; A61M 2039/0264; A61M 2039/0261; A61M 2039/0273; A61M 2039/0276; A61M 2039/0223;
(Continued)

(56) References Cited

U.S. PATENT DOCUMENTS

| | | | |
|---|---|---|---|
| 5,695,471 | A | 12/1997 | Wampler |
| 5,888,242 | A | 3/1999 | Antaki et al. |

(Continued)

FOREIGN PATENT DOCUMENTS

| | | | | |
|---|---|---|---|---|
| EP | 0367354 | A1 * | 5/1990 | ........ A61M 39/0247 |
| EP | 0808632 | A1 | 11/1997 | |

(Continued)

*Primary Examiner* — Shefali D Patel
*Assistant Examiner* — Avery Smale
(74) *Attorney, Agent, or Firm* — Kilpatrick Townsend & Stockton LLP

(57) ABSTRACT

A fluid treatment system for a percutaneous cable and methods of assembly and use are described herein. In one aspect, the fluid treatment system includes a delivery tube comprising a distal end and a proximal end. The distal end is configured to surround at least a portion of the percutaneous cable. The percutaneous cable extends from within a patient to outside the patient through tissue at an exit site. The proximal end is connectable to a fluid source. Fluid from the fluid source is configured to be delivered to the exit site through the delivery tube. The fluid treatment system includes an anchor coupleable to the percutaneous cable to secure the percutaneous cable to the tissue at the exit site.

21 Claims, 5 Drawing Sheets

(51) Int. Cl.
  *A61M 60/00* (2021.01)
  *A61M 60/871* (2021.01)
  *A61M 1/00* (2006.01)
  *A61M 60/148* (2021.01)

(52) U.S. Cl.
  CPC ........ *A61M 60/148* (2021.01); *A61M 60/871*
   (2021.01); *A61M 1/0058* (2013.01); *A61M*
   *2039/0282* (2013.01)

(58) Field of Classification Search
  CPC .. A61M 2039/0232; A61M 2039/0258; A61M
   2039/0294; A61M 2210/12; A61M
   2210/125; A61M 2205/04; A61B
   2218/007
  See application file for complete search history.

(56) References Cited

U.S. PATENT DOCUMENTS

| | | | |
|---|---|---|---|
| 5,904,646 | A | 5/1999 | Jarvik |
| 6,071,093 | A | 6/2000 | Hart |
| 6,116,862 | A | 9/2000 | Rau et al. |
| 6,186,665 | B1 | 2/2001 | Maher et al. |
| 6,234,772 | B1 | 5/2001 | Wampler et al. |
| 6,264,635 | B1 | 7/2001 | Wampler et al. |
| 6,688,861 | B2 | 2/2004 | Wampler |
| 6,991,595 | B2 | 1/2006 | Burke et al. |
| 7,699,586 | B2 | 4/2010 | LaRose et al. |
| 7,976,271 | B2 | 7/2011 | LaRose et al. |
| 7,997,854 | B2 | 8/2011 | LaRose et al. |
| 8,007,254 | B2 | 8/2011 | LaRose et al. |
| 8,152,493 | B2 | 4/2012 | LaRose et al. |
| 8,323,174 | B2 | 12/2012 | Jeevanandam et al. |
| 8,449,444 | B2 | 5/2013 | Poirier |
| 8,506,471 | B2 | 8/2013 | Bourque |
| 8,562,508 | B2 | 10/2013 | Dague et al. |
| 8,597,350 | B2 | 12/2013 | Rudser et al. |
| 8,652,024 | B1 | 2/2014 | Yanai et al. |
| 8,657,733 | B2 | 2/2014 | Ayre et al. |
| 8,668,473 | B2 | 3/2014 | LaRose et al. |
| 2003/0176835 | A1* | 9/2003 | Yamazaki ........... A61M 60/122 604/93.01 |
| 2005/0071001 | A1 | 3/2005 | Jarvik |
| 2006/0025749 | A1* | 2/2006 | Moenning ............ A61M 39/02 604/506 |
| 2007/0078293 | A1 | 4/2007 | Shambaugh, Jr. et al. |
| 2007/0167926 | A1* | 7/2007 | Blott .................. A61M 1/0088 604/304 |
| 2008/0021394 | A1 | 1/2008 | LaRose et al. |
| 2009/0203957 | A1 | 8/2009 | LaRose et al. |
| 2012/0046514 | A1 | 2/2012 | Bourque |
| 2012/0046515 | A1* | 2/2012 | Woo ...................... A61M 1/122 600/16 |
| 2012/0095281 | A1 | 4/2012 | Reichenbach et al. |
| 2012/0149229 | A1* | 6/2012 | Kearsley ............. A61M 1/122 439/339 |
| 2013/0096364 | A1 | 4/2013 | Reichenbach et al. |
| 2013/0121821 | A1 | 5/2013 | Ozaki et al. |
| 2013/0127253 | A1 | 5/2013 | Stark et al. |
| 2013/0170970 | A1 | 7/2013 | Ozaki et al. |
| 2013/0225909 | A1 | 8/2013 | Dormanen et al. |
| 2013/0314047 | A1 | 11/2013 | Eagle et al. |
| 2016/0064117 | A1 | 3/2016 | Romero et al. |
| 2017/0209344 | A1* | 7/2017 | Babbs ................. A61J 15/0069 |

FOREIGN PATENT DOCUMENTS

| | | |
|---|---|---|
| EP | 1344539 A2 | 9/2003 |
| FR | 1491221 A | 8/1967 |
| WO | 2012024567 A1 | 2/2012 |

\* cited by examiner

FLUID TREATMENT SYSTEM FOR A DRIVELINE CABLE AND METHODS OF ASSEMBLY AND USE

CROSS REFERENCE TO RELATED APPLICATIONS

The present application claims the benefit of U.S. Provisional Patent Application Ser. No. 62/612,923 filed Jan. 2, 2018, entitled "FLUID TREATMENT SYSTEM FOR A DRIVELINE CABLE AND METHODS OF ASSEMBLY AND USE" the full disclosure of which is incorporated herein by reference in its entirety for all purposes.

BACKGROUND

This application relates generally to mechanical circulatory support systems, and more specifically relates to fluid treatment systems, such as may be used for a driveline cable for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

The VAD is powered and may also be controlled by a driveline cable that extends from the VAD and through an aperture of the patient to an external power source and/or controller device. The driveline cable may terminate in a connector having a connector adapted to connect to a corresponding connector receptacle of an external power source and/or control unit worn by the patient. Because the driveline cable passes through skin or tissue of the patient, infection around an exit site following implantation of a VAD is a serious complication that may arise in patients with percutaneous driveline cables (e.g., as a result of injury to tissue or skin around the exit site due to tunneling of the driveline cable or movement after implantation). It would be desirable to provide improved systems and methods for the administration of medication or other treatments to treat or manage infections when present, or prevent or reduce the likelihood of infections occurring, associated with such percutaneous driveline cables.

BRIEF SUMMARY

The invention relates generally to mechanical circulatory support systems, and in one embodiment to a fluid treatment systems, such as may be used for a driveline cable for an implantable blood pump. Such fluid treatment systems may be suitable for percutaneous driveline cables that extend outside the body through an incision in the skin. In certain aspects, the invention provides fluid treatment systems suitable for delivering to or removing fluid from incision sites of percutaneous cables for various implantable medical devices. Fluid may be delivered to the incision sites by such fluid treatment systems for improved healing around the incision site, treating or reducing infected tissue, and/or for reducing or preventing the occurrence of infection of the tissue.

In one aspect, a fluid treatment system in accordance with embodiments of the present invention includes a delivery tube comprising a distal end and a proximal end. The distal end is configured to surround at least a portion of a percutaneous cable. The percutaneous cable extends from within a patient to outside the patient through tissue at an exit site. The proximal end is connectable to a fluid source. Fluid from the fluid source is configured to be delivered to the exit site through the delivery tube. The fluid treatment system includes an anchor coupleable to the percutaneous cable to secure the percutaneous cable to the tissue at the exit site. In some embodiments, the delivery tube extends coaxially around the percutaneous cable. The anchor may include at least one of: an outer covering, an adhesive, a sleeve, a tubular device, a filament bundle, or a skirt. Further, the anchor may be implantable subdermally within the tissue surrounding the exit site. The anchor may include a skirt with the skirt including a mesh material coupleable to the percutaneous cable and configured to extend radially away from the percutaneous cable to engage the tissue surrounding the exit site. In certain embodiments, the mesh material includes titanium or nickel titanium wires. In certain embodiments, the fluid treatment system further includes a vacuum assisted closure system configured to remove the fluid delivered to the exit site. In some embodiments, the vacuum assisted closure system is configured to apply negative pressure to the exit site. The delivery tube may be attachable to the percutaneous cable prior to implantation of the percutaneous cable. The delivery tube may be attachable to the percutaneous cable after implantation of the percutaneous cable. In some embodiments, the delivery tube is releasably slidable onto the percutaneous cable.

In another aspect, a blood pump system configured in accordance with embodiments of the present invention includes an implantable blood pump and an implantable cable coupleable to the implantable blood pump. The cable includes a percutaneous portion configured to extend through tissue of a patient at an exit site. The blood pump system further includes a delivery tube including a first end configured to be positioned proximate the exit site and a second end coupleable to a fluid source. The delivery tube is configured to deliver fluid from the fluid source to the exit site. In some embodiments, the blood pump system further includes an anchor configured to secure the cable to the tissue at the exit site. In certain embodiments, the cable comprises a porous cover. In some embodiments, the delivery tube extends coaxially around a portion of the percutaneous portion of the cable. In certain embodiments, the blood pump system further includes a vacuum assisted closure system configured to remove the fluid delivered to the exit site. In some embodiments, the vacuum assisted closure system is configured to apply negative pressure to the exit site.

In yet another aspect, a method of delivering fluid to an exit site of a percutaneous cable is provided in accordance with embodiments of the present invention. The percutaneous cable is coupleable to an implantable medical device and extends through tissue of a patient. The method reduces or prevents infection of tissue at the exit site. The method includes surrounding at least a portion of a percutaneous cable extending through tissue of a patient at an exit site with a delivery tube, positioning a first end of the delivery tube proximate the exit site, connecting a second end of the delivery tube to a fluid source, securing the percutaneous cable to tissue at the exit site, and delivering fluid from the fluid source to the exit site through the delivery tube. Delivering fluid from the fluid source to the exit site through the delivery tube may include delivering fluid between an inner surface of the delivery tube and an outer surface of the percutaneous cable. Surrounding at least a portion of the percutaneous cable with the delivery tube may include coaxially surrounding at least a portion of the percutaneous cable with the delivery tube. In some embodiments, the method further includes removing fluid delivered from the fluid source to the exit site via a vacuum assisted closure system. In some embodiments, the method may include further applying negative pressure to the exit site via a vacuum assisted closure system.

DETAILED DESCRIPTION

Figure 1:
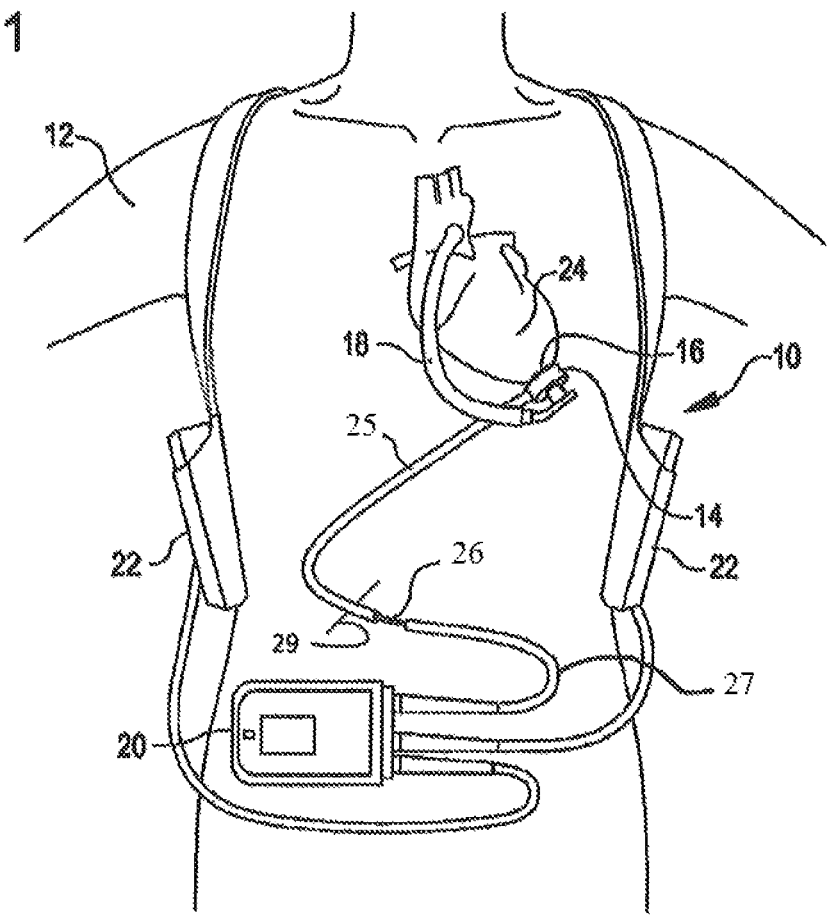
FIG. 1 is an illustration of an implanted mechanical circulatory support system with a driveline cable in accordance with aspects of the invention.

FIG. 1 is an illustration of a mechanical circulatory support system 10 (e.g., a blood pump system) implanted in a patient's body 12. The mechanical circulatory support system 10 comprises an implantable blood pump 14, ventricular cuff 16, outflow cannula 18, system controller 20, and power sources 22. The implantable blood pump 14 may comprise a VAD that is attached to an apex of the left ventricle, as illustrated, or the right ventricle, or two or more VADS attached to both ventricles of the heart 24. The VAD may comprise a centrifugal (as shown) or axial flow pump that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIG. 1, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline cable 25 (e.g., a percutaneous cable or lead) connects the implanted blood pump 14 to the system controller 20, which monitors system 10 operation. The driveline cable 25 may include a percutaneous portion 26 that exits the patient through an exit site 29 (e.g., abdominal aperture) and terminates at in-line connector 28 that connects the percutaneous portion 26 with a modular external cable 27, the other end of the modular external cable 27 being protected within the system controller 20. In some embodiments, prior to the connection of the percutaneous cable portion 26 and the modular cable 27 being made in the operating room, a fluid delivery tube 132 of fluid treatment system 131 in accordance with the present invention (e.g., as described in more detail below with respect to FIGS. 3A-3C) may be installed over a free end of the percutaneous portion 26 and/or the modular cable 27. In other embodiments, the fluid delivery tube 132 may be installed to or over the driveline cable 25 after connection of the percutaneous cable portion 26 and the modular cable 27. Further, in other embodiments, the fluid delivery tube 132 may be installed prior to or after implantation of the driveline cable 25.

Implantable medical pumps (e.g., blood pumps) are used to provide mechanical assistance or augmentation to pumping performed by the left and/or right ventricles of the heart. Due to the pumping volume and constant operation required in such applications, such pumps typically have substantial power requirements, often necessitating a remotely located power source, usually an external power source worn outside the body, such as shown in FIG. 1. Such pumps are typically powered through a driveline cable (e.g., the driveline cable 25), which extends percutaneously through the patient. Because the driveline cable 25 passes through skin or tissue of the patient and may be subject to frequent movement and flexure, infection of tissue at or around the exit site may occur or arise. A fluid treatment system in accordance with the present invention may be installed over the driveline cable 25 to deliver fluid to treat, reduce, or prevent infection of tissue at the exit site 29 of the driveline cable 25. It is further appreciated that a fluid treatment system in accordance with aspects of the invention may be used in various other applications apart from implantable heart pumps. For example, the fluid treatment system 131 may be used to deliver fluid to exit sites of percutaneous cables for any number of implantable medical devices and provide the advantages described herein.

The system controller 20 monitors system operations. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline cable 25, system controller 20 and/or power source 22 may be partially or fully implantable within the patient, as separate components or integrated with the blood pump 14.

Examples of such modifications are further described in U.S. Pat. No. 8,562,508 and U.S. Patent Publication No. 2013/0127253, all of which are incorporated herein by reference for all purposes in their entirety.

Figure 2:
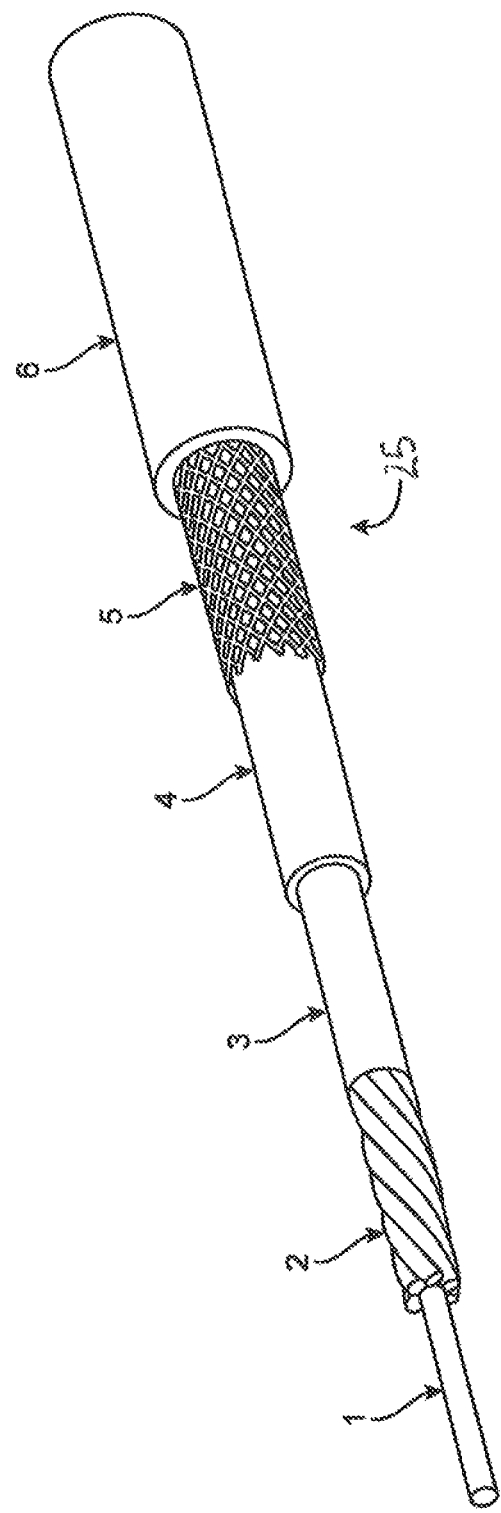
FIG. 2 is an illustration of an example driveline cable in accordance with aspects of the invention.

In the example embodiment shown in FIG. 2, the driveline cable 25 includes a central core 1 around which insulated conductors 2 are wound, each conductor comprising uninsulated wire strands that are loosely packed. Related driveline or percutaneous cables applicable to the present invention are described in greater detail below and in U.S. Patent Publication Nos. 2012/0046515 and 2016/0064117, all of which are incorporated herein by reference for all purposes in their entirety. The exemplary cable 25 may include a redundant set of wires, and accordingly, may include a total of six insulated conductors 2. The insulated conductors may be formed of copper alloy or other suitable material. The central core 1 may be a polyethylene strength member and the conductors 2 may be wound at a 1.00 inch pitch or less, preferably a 0.75 pitch or less, such as at a 0.6 inch pitch. Advantageously, the configuration of the conductors allows for tighter wrapping at smaller, tighter pitches that creates a spring-like effect which considerably reduces strain forces and further improves durability. The wound conductors 2 may be surrounded by a polytetrafluoroetheylene (PTFE) layer 3, followed by a polymer layer with moisture ingress resistance properties 4, such as a Bionate® or a PCU (e.g., a thermoplastic polycarbonate-urethane) layer, followed by an aramid armor layer 5, and an outer cover 6. The outer cover 6 may be a silicone jacket or other material permeable to fluids, porous and configured to allow ingrowth of the patient's biological tissue that contacts the outer cover 6. Providing a permeable and porous outer cover 6 may provide improved distribution of fluid delivered to the exit site 29 and/or vacuum assisted treatments about the exit site 29 (e.g., as described in more detail below with respect to FIG. 5).

Figure 3A:
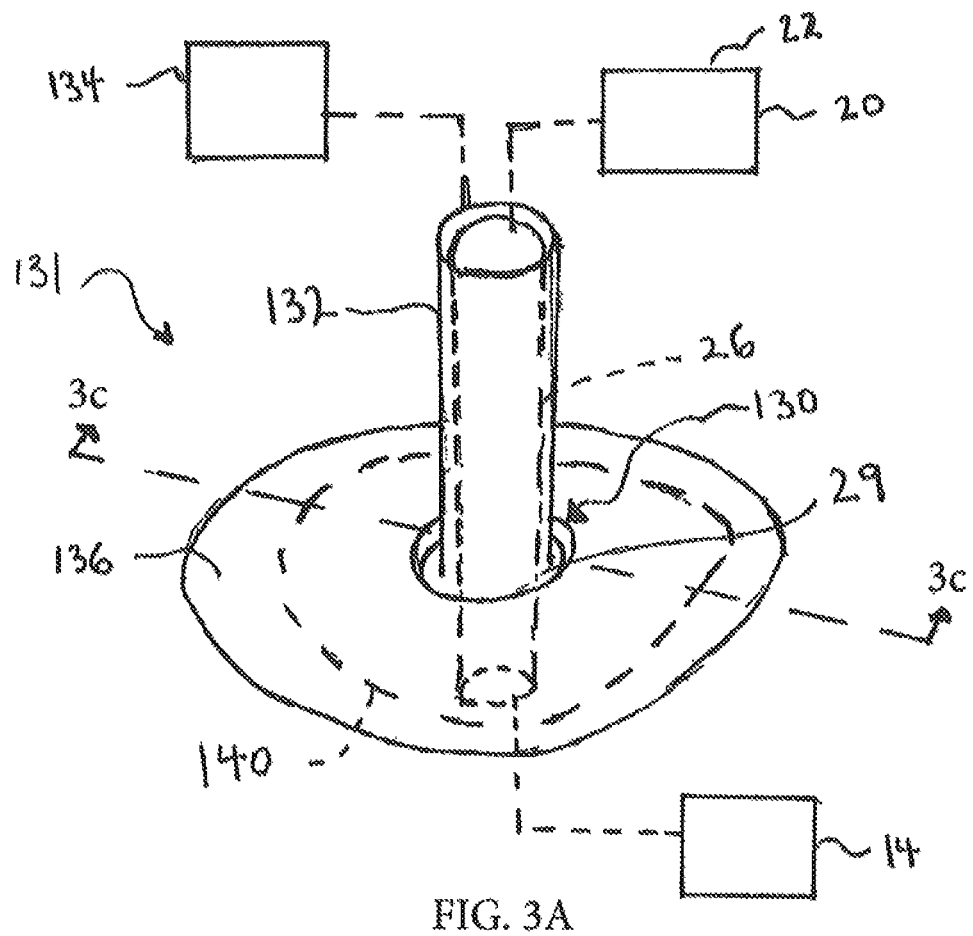
FIG. 3A is an illustration of an example fluid treatment system for a driveline cable in accordance with aspects of the invention.
Figure 3B:
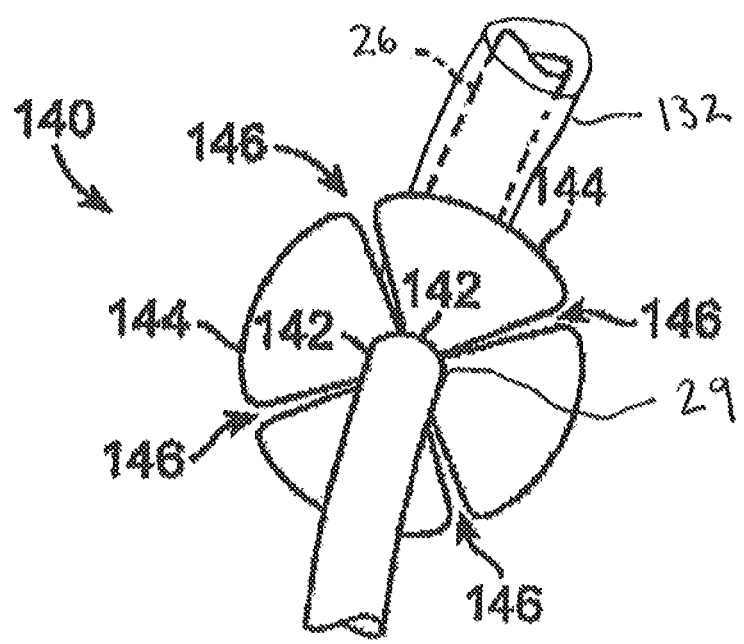
FIG. 3B is bottom perspective view of the example fluid treatment system of FIG. 3A.
Figure 3C:
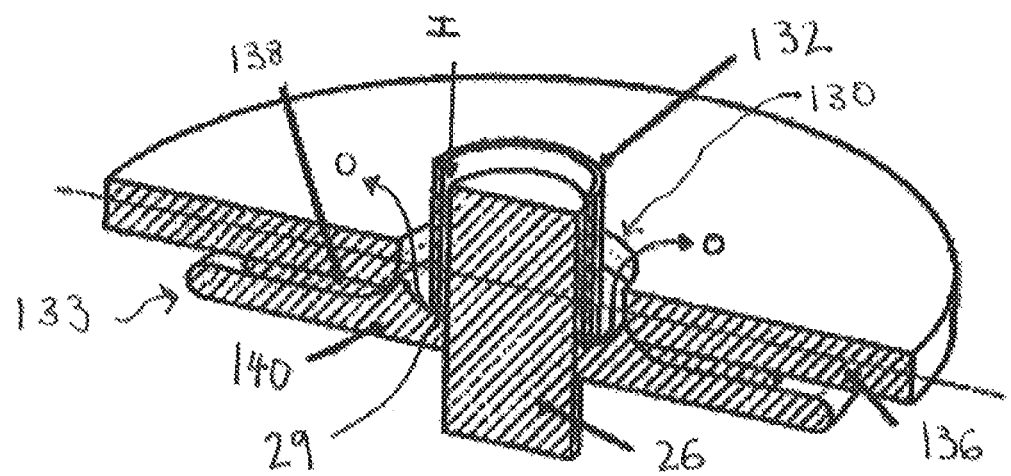
FIG. 3C is a cross-section view of the fluid treatment system of FIG. 3A.

With reference to the embodiments illustrated in FIGS. 3A-3C, the fluid treatment system 131 incudes a delivery tube 132 (e.g., a sleeve, conduit, lumen) and a fluid source 134. The delivery tube 132 may be constructed of polymers (e.g., silicone or polyurethane blends) and/or plastic (e.g., acetal, acrylic). In some embodiments, different portions of the delivery tube 132 may include different materials. For example, a skin interfacing portion may be constructed of a polymer and a fluid delivery portion may be made from harder plastic materials. The delivery tube 132 includes a distal end, a proximal end, and a length therebetween. The distal end of the delivery tube 132 surrounds at least a portion of the driveline cable 25 (e.g., the percutaneous portion 26) when the fluid treatment system 131 is installed. In some embodiments, the delivery tube 132 extends coaxially around a portion of the driveline cable 25 (e.g., the percutaneous portion 26). As illustrated, the percutaneous portion 26 of the driveline cable 25 extends from within a patient to outside the patient through tissue 130 at the exit site 29 for connecting an external controller 20 or power source 22 to the blood pump 14 as described in more detail above. The proximal end of the delivery tube 132 is connected or configured to be connected to a fluid source 134 (e.g., a fluid or solution bag). Fluid (e.g., antibiotic, saline, tissue medium containing protein growth factors such as FGF, cleaning solution, or other solutions) from the fluid source 134 may be delivered to the exit site 29 for improved healing around the exit site 29, treating or reducing infected tissue, and/or for reducing or preventing the occurrence of infection of the tissue. The fluid source 134 may include a mechanism for delivering fluid to the exit site 29 including, for example, a syringe or other needle assembly, a pump, or gravity drip assembly. Further, the fluid treatment system 131 may include an anchor 140 or other securement device (e.g., sutures, adhesives) coupleable to the driveline cable 25 to secure the driveline cable 25 to the tissue 130 at the exit site 29 (e.g., as described in more detail below with respect to FIGS. 3B-3C). The anchor 140 may also provide a seal to the driveline cable 25 at the exit site 29 to reflect or direct delivered fluid outward away from the exit site 29. In this manner, the anchor 140 may provide both sealing and securing features.

As illustrated in FIG. 3C, fluid inflow to and outflow from the exit site 29 are identified by arrows I and O, respectively. For example, fluid may be delivered from the fluid source 134 to the exit site 29 between an inner surface of the delivery tube 132 and an outer surface of the driveline cable 25. After reaching the exit site 29, the delivered fluid may be reflected or otherwise directed outward away from exit site 29 by, for example, the anchor 140 or other sealing device. The delivered fluid may be drained or removed passively or actively. For example, the delivered fluid may be drained via gravity and evacuated to or by pouches, bags, gauze pads or other dressings to collect the outflow of fluid. In other embodiments, the delivered fluid and other debris may be removed via a vacuum assisted closure system 166 (e.g., as described in more detail below with respect to FIG. 5) or other suitable suction or drainage system.

The fluid treatment system 131 (e.g., the delivery tube 132, vacuum assisted closure system 166, or other components) may be installed prior to, during, and/or after implantation of the mechanical circulatory system 10, and more specifically, the driveline cable 25. For example, in some embodiments, the fluid treatment system 131 is installed as part of a manufacturing process (e.g., at a factory) prior to implantation of the system 10 by a clinician or other medical personnel. In other embodiments, the fluid treatment system 131 is installed by a clinician or other medical personnel during and/or after an implantation procedure of the mechanical circulatory system 10. The delivery tube 132 may be slidably installed onto and/or translatable axially relative to at least a portion of the driveline cable 25 (e.g., to be moved into a desired position relative the driveline cable 25 at the exit site 29). In some embodiments, the delivery tube 132 may be threaded onto the driveline cable 25. In other embodiments, the delivery tube 132 may be secured in position (e.g., to the driveline cable 25) with an adhesive or other mechanical attachment. In some embodiments, the delivery tube 132 may be configured to be installed permanently onto the driveline cable 25 (e.g., configured to remain installed while the driveline cable 25 is implanted within a patient). In other embodiments, the fluid treatment system 131 may be configured to be installed temporarily (e.g., to provide treatment by delivering fluid and then removable once treatment, a treatment session, or healing is completed).

Fluid delivered to the exit site 29 may promote healing. For example, the fluid may include antibiotics or other medication delivered to the exit site 29. The fluid may also flush the exit site 29 to remove undesirable fluid, discharge, bacteria, or other debris. Therefore, the fluid treatment system 131 may deliver fluid to treat or reduce infection when present at the exit site 29. The fluid treatment system 131 may also deliver fluid to prevent or reduce the occurrence of infection at the exit site 29. In some embodiments, fluid is configured to be delivered and removed continuously or permanently (e.g., while the driveline cable 25 is implanted in the patient). Fluid may be delivered and removed at a relatively slow flow rate (e.g., on the order of milliliters per day). For example, a continuous drip-type fluid delivery assembly may be provided. In other embodiments, fluid is delivered and removed semi-continuously or over a set period of time (e.g., minutes, hours, days, etc). For example, fluid may be delivered and removed as part of a prescribed treatment cycle or cycles over set periods of time. A specific period of time or flow rate of fluid delivery and removal may be configured by the patient or medical personnel. For example, the fluid source 134 may include a valve that may be opened or closed as desired to release fluid to the delivery site 29. In certain embodiments, two or more fluids may be delivered. For example, a saline or other cleaning solution may be delivered to flush the exit site 29 prior to delivering fluid containing antibiotics or other medication to the exit site 29. Fluid to flush the exit site may be for a discrete period of time (e.g., seconds, minutes) and at a relatively faster flow rate (e.g., on the order of milliliters per sec) relative to delivering an antibiotic or other fluid with medication.

With reference to FIGS. 3B-3C, the anchor 140 may be a subdermal anchor coupled to the percutaneous driveline cable 25. The subdermal anchor 140 may be configured for implantation within the tissue 130 surrounding the exit site 29. The subdermal anchor 140 is attached to and extends radially away from the percutaneous cable 25, and is configured for coupling to one or more subdermal layers under the skin 136 of a patient. In some embodiments, the subdermal anchor 140 is a porous device configured to allow ingrowth 138 of the tissue 130 surrounding or in the vicinity of the exit site 29. In other embodiments, the subdermal anchor 140 is substantially non-porous and comprises barbs or hooks configured to engage the surrounding tissue 130. In some embodiments, a subdermal anchor 140, such as a skirt (FIG. 4), may be implanted in a subdermal pocket 133 (e.g., below the skin surface 136) made in advance by an incision into the tissue 130 surrounding the exit site 29. In other embodiments, a subdermal pocket 133 is not made ahead of time and a subdermal anchor, such as a filament bundle or barbed filament, is sutured against the surrounding tissue 130 using a needle. Related anchors and other securement devices applicable to the present invention are described in greater detail below (e.g., with respect to FIG. 4) and in U.S. Patent Publication No. 2012/0046515, which has been incorporated by reference above. For example, other securement devices may include one or more of: an adhesive, a tubular securement device, a sleeve, or, a filament bundle. Such securement devices may also provide sealing to reflect or direct delivered fluid from the fluid treatment system 131 outward away from the exit site 29.

As illustrated, in some embodiments, the subdermal anchor 140 may be in the form of a porous skirt attached to and extending radially away from the driveline cable 25 (for example, extending radially away from the longitudinal length or axis of the cable). The skirt comprises an inner edge 142 attached to the cable 25 and an outer edge 144 opposite the inner edge 142. The skirt may be a thin, flexible, and substantially flat material. Suitable materials include without limitation a mesh of titanium or nickel titanium wires and a mesh of synthetic polymer monofilament, such as polypropylene filament. Conventional mesh material used for hernia repair may also be used for the skirt. The skirt may have one or more radial slits 146 to facilitate placing the skirt in a folded or collapsed configuration. The gaps within the mesh and the slits 146 allow for better blood supply to the epidermis than if the skirt 146 were non-porous and had no slits. For example, the porosity of the skirt allows for tissue ingrowth 138. Tissue ingrowth includes tissue adhesion to and encapsulation of the skirt 140.

Figure 4:
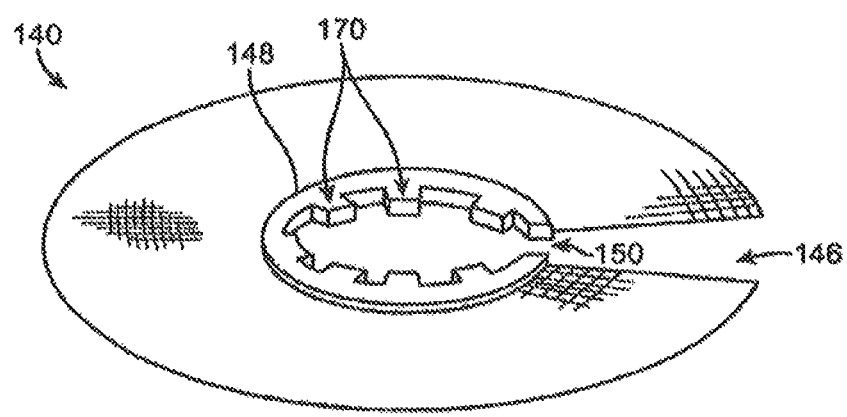
FIG. 4 is an illustration of an example anchor for a driveline cable in accordance with aspects of the invention.

The inner edge 142 of the skirt may be moveable so that after the percutaneous driveline cable 25 is fed through the exit site 29, the inner edge 142 may be moved axially on the cable 25 until the skirt is at or near the exit site 29. Referring to FIG. 4, to allow such movement, the inner edge 142 of the skirt may be attached to a holding device, such as a split ring 148, which may be slidable on or removable from the cable 25. A cut 150 through the split ring 148 corresponds in position to the single slit 146 in the skirt. The cut 150 forms opposite ends on the split ring 148 which are spaced apart from each other by a distance that is smaller than the outer diameter of the cable 25. In use, the split ring 148 may be bent to temporarily spread apart the split ring ends and thereby allow the split ring to be mounted around the cable 25 at any axial position on the cable and at any time, before or after the cable has been fed through the exit site 29. The split ring 148 may clamp tightly around the percutaneous driveline cable 25. In some embodiments, as shown in FIG. 4, the split ring 148 comprises a plurality of teeth 170 that face radially inward. The teeth 170 are configured to clamp down onto the percutaneous driveline cable 25 and prevent axial movement of the split ring 148.

Figure 5:
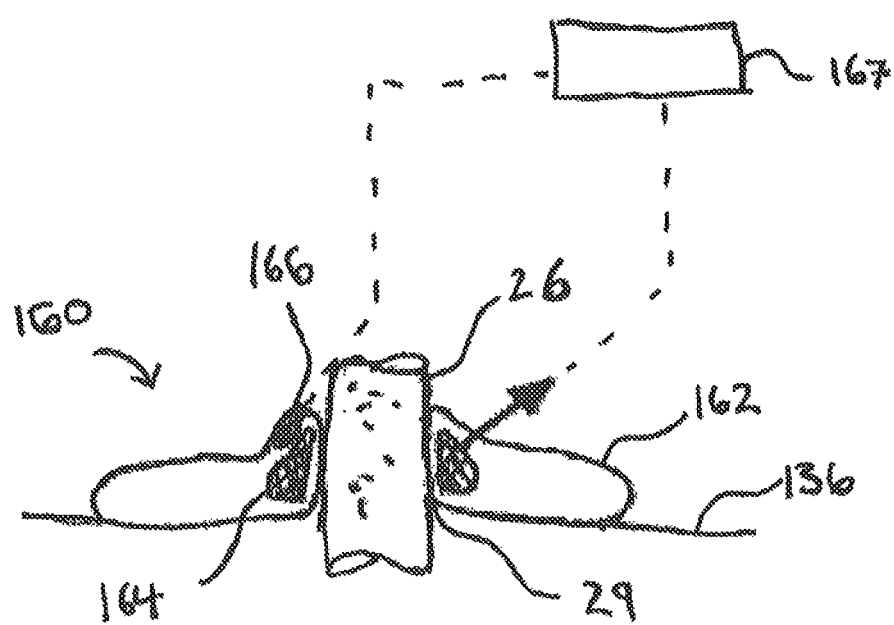
FIG. 5 illustrates a cross-section of a vacuum assisted closure system for a driveline cable in accordance with aspects of the invention.

As illustrated in FIG. 5, a vacuum assisted closure system 160 may be provided for use with the fluid treatment system 131 or as a stand-alone system (FIG. 5) according to certain embodiments described herein. The vacuum assisted closure system 160 may be configured to treat infection or promote wound healing by providing fluid delivery, vacuum assisted fluid or wound drainage, and/or vacuum assisted wound closure (e.g., via negative pressure wound therapy). For example, in some embodiments, the vacuum assisted closure system 160 may include one or more Tegaderm™ patches or other suitable wound dressings 162 adhered or otherwise attached to skin 136 of a patient. When used in combination with the fluid treatment system 131, the wound dressings 162 may be attached or secured to form a seal around the delivery tube 132 (not illustrated) rather than directly to the percutaneous portion 26 of the driveline cable 25 as illustrated in FIG. 5 and described in more detail below. In some embodiments, the vacuum assisted closure system 160 may also include additional foam or other suitable dressings positioned at or within the exit site 29 to aid in wound healing with the system 160.

In certain embodiments, two or more wound dressings 162 may be attached to the skin 136 of a patient and around (e.g., on opposing sides of) the driveline cable 25. In this manner, the dressings 162 and vacuum assisted closure system 160 may be attached after implantation of the driveline cable 25 without having to disconnect the driveline cable 25. In other embodiments, a single dressing 162 may be attached to the skin 136 of a patient with an aperture to allow the driveline cable 25 to extend therethrough rather than using two or more dressings attached together around the cable 25. As described in more detail above, the driveline cable 25 may include a porous cover to induce tissue ingrowth and allow improved fluid dispersion or distribution around the exit site 29. The two or more dressings 162 may include a vacuum assist port 164. The vacuum assist port 164 may extend circumferentially through the dressing(s) 162 around the driveline cable 25. The vacuum assist port 164 is connected to a vacuum source or other suction device 167. As illustrated, the vacuum source 167 may provide suction or negative pressure for wound, fluid, or discharge drainage or removal and/or wound closure. The one or more dressings 162 may also include a valve or fluid port 166. The fluid port 166 may also be connected to the vacuum source 167 or a separate fluid source (e.g., fluid source 134) configured to deliver fluid for flushing or treating the exit site 29. Therefore, vacuum assisted wound therapy (closure or drainage) and fluid delivery, drainage, or removal may be provided by the vacuum assisted closure system 160 either alone or in combination with the fluid treatment system 131.

Although the invention is described in terms of a fluid treatment system for a VAD, one will appreciate that the invention may be applied equally to other implantable medical devices with percutaneous cables.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A treatment fluid supply system for an implantable medical device, the treatment fluid supply system comprising:
    a percutaneous cable configured to transfer electric power supplied by a power source disposed external to a patient to the implantable medical device, wherein the percutaneous cable is configured for implantation into the patient to extend from within the patient to outside the patient through an exit site aperture in a tissue surrounding the exit site aperture;
    a subdermal anchor interfaced with and extending radially away from the percutaneous cable, wherein the subdermal anchor is configured for implantation within the tissue surrounding the exit site aperture and coupling to one or more subdermal layers of skin of the patient; and
    a delivery tube attached to the percutaneous cable, wherein the delivery tube comprises a distal end, wherein the delivery tube surrounds a percutaneous portion of the percutaneous cable that extends through the exit site aperture, wherein the delivery tube is connectable to a fluid source to receive a flow of a treatment fluid from the fluid source, and wherein the delivery tube is configured to discharge the flow of the treatment fluid out of the distal end of the delivery tube onto the subdermal anchor for redirection by the subdermal anchor so as to flow out from the exit site aperture in contact with the tissue surrounding the exit site aperture.

2. The treatment fluid supply system of claim 1, wherein the delivery tube extends coaxially around the percutaneous portion of the percutaneous cable.

3. The treatment fluid supply system of claim 2, wherein the subdermal anchor comprises at least one of: an outer covering, an adhesive, a suture, a sleeve, a tubular device, a filament bundle, and a skirt.

4. The treatment fluid supply system of claim 2, wherein the subdermal anchor comprises a skirt configured to extend radially away from the percutaneous cable to engage the tissue surrounding the exit site aperture, and wherein the skirt comprises a mesh material.

5. The treatment fluid supply system of claim 4, wherein the mesh material comprises titanium or nickel titanium wires.

6. The treatment fluid supply system of claim 1, further comprising a vacuum assisted closure system configured to remove at least a portion of the flow of the treatment fluid that flows out of the exit site aperture.

7. The treatment fluid supply system of claim 1, further comprising a vacuum assisted closure system configured to apply negative pressure to the tissue surrounding the exit site aperture.

8. The treatment fluid supply system of claim 1, wherein the delivery tube is attachable to the percutaneous cable prior to implantation of the percutaneous cable.

9. The treatment fluid supply system of claim 1, wherein the delivery tube is attachable to the percutaneous cable after implantation of the percutaneous cable.

10. The treatment fluid supply system of claim 1, wherein the delivery tube is releasably slidable onto the percutaneous cable.

11. The treatment fluid supply system of claim 1, wherein the subdermal anchor comprises a seal that is interfaced with the percutaneous cable and configured to redirect the flow of the treatment fluid discharged from the distal end so as to flow out of the exit site aperture in contact with the tissue surrounding the exit site aperture.

12. A blood pump system comprising:
    an implantable blood pump;
    an implantable cable coupleable to the implantable blood pump, wherein the implantable cable comprises a percutaneous portion that is configured to extend from within a patient to outside the patient through an exit site aperture in a tissue surrounding the exit site aperture;
    a subdermal anchor interfaced with and extending radially away from the implantable cable, wherein the subdermal anchor is configured for implantation within the tissue surrounding the exit site aperture and coupling to one or more subdermal layers of skin of the patient; and
    a delivery tube comprising a first end portion coupled with the percutaneous portion so as to extend into the exit site aperture and a second end coupleable to a fluid source, wherein the delivery tube is configured to receive a flow of a treatment fluid from the fluid source and discharge the flow of the treatment fluid onto the subdermal anchor for redirection by the subdermal anchor so as to flow out from the exit site aperture in contact with the tissue surrounding the exit site aperture.

13. The blood pump system of claim 12, wherein the subdermal anchor comprises a seal that is interfaced with the implantable cable and configured to redirect the flow of the treatment fluid discharged from the delivery tube so as to flow out of the exit site aperture in contact with the tissue surrounding the exit site aperture.

14. The blood pump system of claim 12, wherein the implantable cable comprises a porous cover.

15. The blood pump system of claim 12, wherein the delivery tube extends coaxially around a portion of the percutaneous portion of the implantable cable.

16. The blood pump system of claim 12, further comprising a vacuum assisted closure system configured to remove at least a portion of the flow of the treatment fluid discharged from the delivery tube.

17. A method of discharging a flow of a treatment fluid onto a tissue surrounding an exit site aperture of a percutaneous cable coupled to an implanted medical device to reduce or prevent infection of the tissue surrounding the exit site aperture, the method comprising:

surrounding at least a portion of the percutaneous cable that extends from within a patient to outside of the patient through the exit site aperture in the tissue surrounding the exit site aperture with a distal end portion of a delivery tube;

supporting the distal end portion of the delivery tube proximate the exit site aperture;

receiving the flow of the treatment fluid into the delivery tube, wherein the flow of the treatment fluid is supplied by a fluid source;

restraining the percutaneous cable via a subdermal anchor coupled to one or more subdermal layers of skin of the patient surrounding the exit site aperture; and discharging the flow of the treatment fluid from the distal end portion into the exit site aperture onto the subdermal anchor for redirection by the subdermal anchor so as to flow out from the exit site aperture in contact with the tissue surrounding the exit site aperture.

18. The method of claim 17, further comprising conveying the flow of the treatment fluid between an inner surface of the delivery tube and an outer surface of the percutaneous cable.

19. The method of claim 17, wherein the delivery tube coaxially surrounds at least the portion of the percutaneous cable.

20. The method of claim 17, further comprising removing at least a portion of the flow of the treatment fluid discharged from the distal end portion via a vacuum assisted closure system.

21. The method of claim 17, further comprising applying negative pressure to the tissue surrounding the exit site aperture via a vacuum assisted closure system.

* * * * *